United States Patent [19]
Tamai et al.

[11] 3,983,175
[45] Sept. 28, 1976

[54] PROCESS FOR THE PRODUCTION OF A SUBSTITUTED KETONE

[75] Inventors: Yoshin Tamai; Takashi Nishida; Fumio Mori, all of Kurashiki; Yoshiaki Omura, Mitsu; Masahisa Tanomura, Kurashiki; Takeo Hosogai, Kiyone; Yoichi Ninagawa; Kazuo Itoi, both of Kurashiki, all of Japan

[73] Assignee: Kuraray Co., Ltd., Kurashiki, Japan

[22] Filed: May 29, 1975

[21] Appl. No.: 581,841

Related U.S. Application Data

[63] Continuation-in-part of Ser. No. 417,201, Nov. 19, 1973, abandoned.

[52] U.S. Cl. .................. 260/586 R; 260/590 R; 260/591; 260/593 R; 260/592
[51] Int. Cl.² .................................. C07C 45/00
[58] Field of Search ........... 260/586 R, 590 R, 591, 260/593 R, 590, 593, 592

[56] References Cited
UNITED STATES PATENTS

| | | |
|---|---|---|
| 3,668,255 | 6/1972 | Meuly et al. .................. 260/593 R |
| 3,701,814 | 10/1972 | Shilling ........................ 260/593 R |

FOREIGN PATENTS OR APPLICATIONS

| | | |
|---|---|---|
| 2,356,866 | 11/1973 | Germany ........................ 260/593 |

*Primary Examiner*—James O. Thomas, Jr.
*Assistant Examiner*—James H. Reamer
*Attorney, Agent, or Firm*—Bacon & Thomas

[57] ABSTRACT

A process for producing substituted ketones is disclosed comprising reacting an organic halide with a ketone which has a replaceable hydrogen atom on the carbon atom in the α-position to the carbonyl group, in the presence of an aqueous alkali metal hydroxide and at least one basic nitrogen catalyst such as certain primary amines, secondary amines, tertiary amines, quaternary ammonium salts or betaine-type quaternary ammonium salts.

23 Claims, 5 Drawing Figures

PROCESS FOR THE PRODUCTION OF A SUBSTITUTED KETONE

This application is a continuation-in part of the copending application Ser. No. 417,201, filed Nov. 19, 1973 now abandoned.

BACKGROUND OF THE INVENTION

1. Field of the Invention

The present invention relates to a catalytic process for the prduction of a substituted ketone by reacting an organic halide with a ketone in the presence of an alkali metal hydroxide with the elimination of hydrogen halide. More particularly, this invention relates to a process for the production of a substituted ketone which comprises reacting an organic halide with a ketone containing an active hydrogen atom at the α-position to the carbonyl group in the presence of an aqueous alkali metal hydroxide and a specific nitrogen base catalyst.

2. Description of the Prior Art

The reaction between an organic halide and a ketone containing an active hydrogen atom at the α-position to the carbonyl group in the presence of an alkali metal hydroxide and a catalyst has heretofore been known. This reaction is represented by the following reaction scheme:

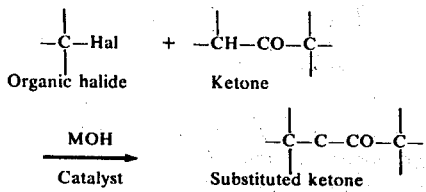

where M is an alkali metal.

Since water is produced in this reaction, it is practically impossible to carry out the reaction under absolutely anhydrous conditions, It has heretofore been generally held that one must strictly avoid adding a considerable amount of water to the reaction system at the beginning of the reaction since the presence of water in the reaction system markedly effects the yield of the product. Therefore, the addition of water with the reactants has been restricted in general, and the alkali metal hydroxide has been added in solid form to the reaction system. For example, it is described in Japanese Patent Publication No. 22,251/1965, which corresponds to U.S. Pat. No. 3,668,255, that the dryness of the reactants is not critical when the reaction is conducted with an amine catalyst but in most cases the reaction proceeds without difficulty even in the presence of not more than 2 moles of water per 1 mole of the organic halide. However, all of the reactions described in said patents are effected substantially under anhydrous conditions.

The present inventors illustratively effected the following experiment. When prenyl chloride was reacted with acetone in the presence of an alkali metal hydroxide, the very small amount of water contained in the acetone inhibited the progress of the reaction, and an amount of water contained in such reactants as potassium iodide, sodium iodide, dimethyl sulfone, sulfolane, tributylphosphine, tributylphosphine oxide, methylamine, dimethylamine, trimethylamine, ethylamine, cyclohexylamine, or ammonium chloride noticeably lowered the yield. Even from the point of view of the economic effects derived from the abridgement of the need for strictly drying the reactants, the allowable water content was only 2.0 moles per 1 mole of the organic halide.

SUMMARY OF THE INVENTION

It has now been surprisingly discovered by the present inventors that the desired substituted ketone can be prepared, substantially without a reduction in yield in comparison with the yield obtained by reaction under anhydrous conditions, and even in increased yields according to the catalyst used, and with good reproducibility, by reacting the organic halide with the ketone in water in the presence of a certain nitrogen base catalyst, wherein the molar ratio water/organic halide is not less than 2.5; the molar ratio alkali metal hydroxide/water is not less than 0.3; and the molar ratio alkali metal hydroxide/organic halide is not less than 2.0.

The present invention has many industrially advantageous points as follows: good reproducibility of reaction rates; reaction at a uniform reaction rate; therefore, easy control of reaction at a uniform reaction rate; therefore, easy abridgement in apparatus; availability in continuous operations; etc.

In addition to the excellent reproducibility and many other advantageous points based thereon, the process of this invention also provides the following other advantages.

1. The alkali metal hydroxide need not be used in the form of powders or flakes but rather, pellets thereof or aqueous solutions thereof can be employed, both of which are available industrially and inexpensively. The fact that the alkali metal hydroxide can be used in the form of an aqueous solution simplifies the problem of adding the alkali metal hydroxide to the reaction system and contributes to improvements in operations and environmental effects.
2. When the reaction is carried out under total anhydrous conditions or substantially anhydrous conditions, by using solid alkali metal hydroxide, the solid alkali metal hydroxide might have a tendency to precipitate or stick to the bottom of the reactor during reaction whereby the alkali metal hydroxide is not used effectively. In such a case, some special operational considerations, particularly stirring, are required. Such problems are eliminated by using an aqueous solution of the alkali metal hydroxide.
3. The allowable water content contained in the reactants increases markedly, and so the unreacted ketone compound can be recovered and reused economically to a remarkable extent.
4. In most cases, the amount of the ketone used can be lowered in comparison with known methods.

DESCRIPTION OF THE PREFERRED EMBODIMENTS

Figure 1:
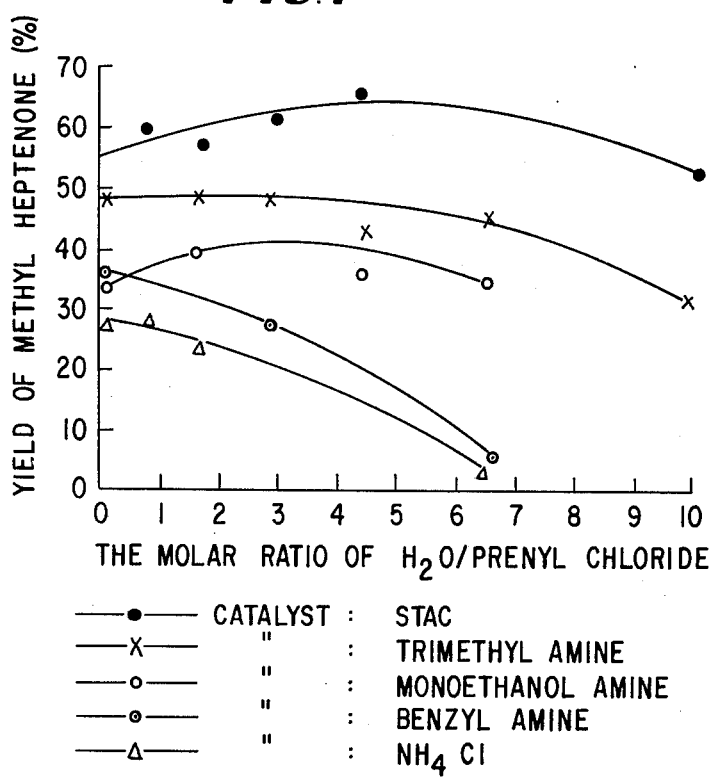
FIGS. 1, 2 and 3 show the effects of the water/organic halide molar ratio, the alkali metal hydroxide/organic halide molar ratio and the ketone/organic halide molar ratio on the yield of substituted ketone, respecively.

The nitrogen base catalyst which is used in the present invention may be any of the following six types of catalysts, or mixtures of the various types:

1. Primary amines represented by the formula: $R_1NH_2$, wherein $R_1$ represents an alkyl group having at least four carbon atoms, a substituted alkyl group having at least four carbon atoms, or acid salts thereof. There is no maximum number of carbon atoms for such alkyl groups, and the substituent or substituents on the alkyl group are not particularly limited, typical examples being hydroxy, amino, alkoxy and acyl groups. Acid salts can also be employed, such as the hydrochloride and nitrate salts, etc. Specific examples of primary amines are as follows: butylamine, isobutylamine, pentylamine, hexylamine, octylamine, decylamine, laurylamine, tridecylamine, tetradecylamine, cetylamine, stearylamine, and their hydrochloride, nitrate, sulfate phosphate and acetate salts.

2. Primary amines represented by the formula:: $Z-(CH_2)_n-NH_2$ wherein Z represents a hydroxy or amino group (i.e., $NH_2$), and typical examples of such primary amines are monoethanolamine, monopropanolamine, ethylenediamine, propylenediamine, and their acid salts such as the hyrochloride, nitrate, sulfate, phosphate and acetate salts thereof.

3. Secondary amines represented by the formula: $R_2NHR_3$ wherein $R_2$ and $R_3$ each represents an alkyl group (containing a minimum of 1 carbon atom with no maximum), cycloalkyl groups containing at least 6 carbon atoms (with no maximum) or aralkyl groups containing at least 7 carbon atoms (with no maximum), and in addition, such alkyl groups substituted by various substituents, the particular substituent not being critical. Examplary substituents are hydroxy, amino, alkoxy and acyl groups. $R_2$ and $R_3$ may not each simultaneously be a methyl group. Also included in this classification of secondary amines are the acid salts thereof. Typical examples of secondary amines satisfying the above formula are as follows: diethylamine, dipropylamine, diisopropylamine, dibutylamine, diisobutylamine, dipentylamine, dihexylamine, diheptylamine, dioctylamine, diundecylamine, dilauryl amine, methylpropylamine, methylbutylamine, methylisobutylamine, methylamylamine, methyldodecylamine, ethylpropylamine, ethylisopropylamine, ethylbutylamine, ethylisobutylamine, ethylhexadecylamine, propylbutylamine, butylisobutylamine, butylhexadecylamine, diethanolamine, amines of the formula:

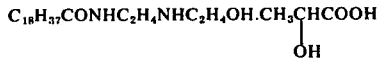

and acid salts thereof (e.g., hydrochloride, nitrate, sulfate, phosphate and acetate salts).

4. Tertiary amines represented by the formula:

wherein $R_4$, $R_5$ and $R_6$ each represents an unsubstituted alkyl group (having a minimum of 1 carbon atom with no maximum carbon atom number), a cycloalkyl group containing at least 6 carbon atoms, an aralkyl group containing at least 7 carbon atoms, or a subsituted alkyl group with the substituents not being critical. Typically, the substituent is a hydroxy, amino, alkoxy, or acyl group, etc. Also included in this classification of tertiary amines are the acid salts of the above compounds, such as the hydrochloride salts thereof. The only proviso is that $R_4$, $R_5$ and $R_6$ may not each be simultaneously methyl groups. Typical examples of such tertiary amines are the following: triethylamine, tripropylamine, tributylamine, triisobutylamine, tripentylamine, trihexylamine, triheptylamine, trioctylamine, tricetylamine, dimethylpropylamine, dimethylisopropylamine, dimethylocdetdecylamine, methyldiethylamine, methylethylpropylamine, methylethylbutylamine, methylethylisobutylamine, methylpropyldecylamine, methylbutylisobutylamine, diethylhexadecylamine, ethyldipropylamine, triethanolamine, benzyldimethylamine, lauryldiethanolamine, and acid salts thereof (e.g., hydrochloride, nitrate, sulfate, phosphate and acetate salts.

5. Quaternary ammonium salts represented by the formula:

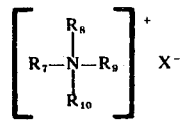

wherein $R_7$, $R_8$, $R_9$ and $R_{10}$ each represents a substituted (the particular substituent not being critical) or unsubstituted alkyl group (having a minimum of 1 with no maximum number of carbon atoms), a cycloalkyl group having at least 6 carbon atoms (with no maximum) or an aralkyl group having at least seven carbon atoms (with no maximum) Typical substituents are hydroxy, amino, alkoxy and acyl groups, etc. The only proviso is that $R_7$, $R_8$, $R_9$ and $R_{10}$ may not each be simultaneously methyl groups. In the above formula, X represents an anion and includes any anion having the capability of forming a quaternary ammonium salt with the ammonium moiety under the aqueous environment and having the capability of forming an alkali metal salts with an alkali metal hydroxide. Typical anions are the following anions: $Cl^-$, $Br^-$, $I^-$, $OH^-$, $NO_3^-$, $ClO_4^-$, $SCN^-$, $CH_3COO^-$,

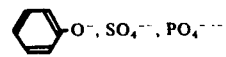
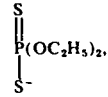

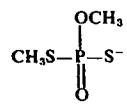
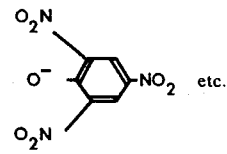
etc.

Typical examples of operable quaternary ammonium salts are the following: tetrapentyl ammonium salt, lauryltrimethylammonium salt, stearyltrimethylammonium salt, stearyldimethylethylammonium salt, cetyltrimethylammonium salt, cetyldimethylethylammonium salt, cetyldimethylbenzyl ammonium salt, benzyltrimethylammonium salt, benzyldimethylethylammonium salt, trilaurylmethylammonium salt, dioctyldimethylammonium salt, didecyldimethylammonium salt, ditetradecyldimethylammonium salt, dicetyldimethylammonium salt, distearyldimethylammonium salt, tetradecyltrimethylammonium salt, dodecylbenzyldimethylammonium salt, octylbenzyldimethylammonium salt, decylbenzyldimethylammonium salt, hexadecylbenzyldimethylammonium salt, and triethylhexylammonium salt.

6. Betaine-type quaternary ammonium salt represented by the formula:

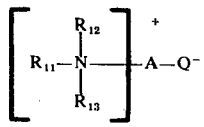

wherein $R_{11}$, $R_{12}$ and $R_{13}$ each represents an unsubstituted or substituted (the particular substituent not being critical) alkyl group (having from a minimum of 1 to no maximum number of carbon atoms). Typical substituents are hydroxy, amino, alkoxy, acyl or acyloxy groups. The only proviso is that said $R_{11}$, $R_{12}$ and $R_{13}$ may not each be simultaneously methyl groups. In the above formula A represents an alkylene group having from 1 to 5 carbon atoms and Q represents $-SO_3$ or $-COO$. Exemplary betaine-quaternary salts are the following:

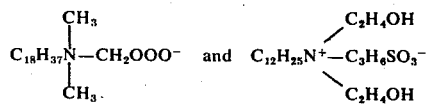

The above types of nitrogen base catalysts may be used alone or in combinations of two or more thereof, if necessary. A suitable amount of the nitrogen base catalyst is ordinarily about 0.05 to 20 mole %, preferably about 0.1 to 10 mole %, based on the number of moles of the organic halide, although the specific amount depends on the exact catalyst selected.

Those compounds which have, in their molecule, at least one radical selected from the group consisting of alkyl groups having 8 to 20 carbon atoms, cycloalkyl groups having 6 to 12 carbon atoms or aralkyl groups having 7 to 12 carbon atoms, are preferred for use as the catalyst in the reaction of the present invention. Thus, in the aforementioned quaternary ammonium salt catalyst (5), for example, each of $R_7$, $R_8$, $R_9$ and $R_{10}$ is selected from the group consisting of an alkyl group having from 8 to 20 carbon atoms, a cycloalkyl group having 6 to 12 carbon atoms, or an aralkyl group having 7 to 12 carbon atoms.

Some of these nitrogen base catalysts used in the present invention shoe higher catalytic potentials than in the reaction under anhydrous conditions and can provide a sufficiently rapid reaction rate even when used in amounts smaller than the amounts used in the reaction under anhydrous conditions. Since in particular, cetyltrimethylammonium salt, cetyldimethylethylammonium salt, lauryldimethylethylammonium salt, stearyltrimethylammonium salt, stearyldimethylethylammonium salt, benzyltrimethylammonium salt and benzyldimethylethylammonium salt, benzyltrimethylammonium salt and benzyldimethylethylammonium salt show very excellent catalytic potentials although they have not been used as catalysts, the object substituted ketone can be obtained in a markedly increased yield even when a smaller amount of catalyst is used, such as 0.1 to 1 mole %, based on the number of moles of the organic halide, compared to the other nitrogen base catalysts.

The mole ratio organic halide/ketone may be from 2/1 to 1/20, preferably about 1/3 to 1/10 in general, although these ranges are not critical and may be exceeded.

One of the important requirements of the present invention is that the reaction can be improved, and the said various advantageous points can be attained. It is particularly preferable for reaction operations and from the view point of reaction yield and reaction economics to add from 2.5 to 10 moles of water per 1 mole of the organic halide from the beginning of the reaction. However, the upper limit of water range to the organic halide is not critical and may be exceeded under the condition that the amount of the alkali metal hydroxide is at least 0.3 mole per 1 mole of water. The process of the invention may be carried out continuously or discontinuously. When said process is carried out continuously, the organic halide may be added dropwise into the circulated mixture comprising the large amount of an aqueous metal hydroxide solution and the ketone to the organic halide added, in the presence of a catalyst. As the result, the extensive order of water to the organic halide may be presented in the reaction system. At the end of the reaction, almost of the organic halide added into the reaction system may be exhausted by the reaction with the ketone prior to decomposition of said organic halide which may be promoted by water, under the conditions described above. An aqueous metal hydroxide solution, unreacted ketone and the catalyst may, in general, be recovered and reused for repeating of said reaction process continuously.

To obtain a good yield of the substituted ketone, the amount of the alkali metal hydroxide is at least 2 moles per 1 mole of the organic halide and at least 0.3 mole per 1 mole of water. The preferred amount of alkali metal hydroxide is about 2.5 to 4 moles per 1 mole of organic halide and about 0.35 to 0.85 mole per 1 mole of water. In general, the amount of alkali metal hydroxide need not be greater than 5 moles per 1 mole of organic halide and 1 mole per 1 mole of water. Satisfactory results can be obtained by using cheap sodium hydroxide as the alkali metal hydroxide, but potassium hydroxide can also be used in lieu of or together with the sodium hydroxide. The alkali metal hydroxide can be added to the reaction system as a solid in the form of optional physical shapes independently from the addition of water, but it is particularly preferable to add a 40 to 65% by weight solution of the alkali metal hydroxide in water to the reaction system, whereby the addition of the alkali metal hydroxide into the reaction system presents little difficulty and provides better operations and less deleterious environmental effects as well as excellent yields of the reaction in general.

The process of the present invention may be effected in the range of temperature from 0° to 150°C., preferably at 40° to 80°C. from the point of view of the relation of reaction temperature to yield, although these ranges are not critical. The reaction may be effected generally at atmospheric pressure as long as the reactants do not boil at the reaction temperature, but the reaction may be effected under superatmospheric or slightly reduced pressure, if necessary. When one or more ingredients among the reactants boil at the reaction temperature, the reaction may be effected in general under refluxing under atmospheric pressure. When starting materials of especially low boiling point are used, the reaction may be effected in a sealed system under superatmospheric pressure.

Although the required reaction time depends on the starting materials, reaction temperature or desired conversion, it is favorable in general to continue the reaction until nearly the entire amount of organic halide is converted. Nearly all the organic halide contained in the reaction system is consumed ordinarily in 10 minutes to 30 – 40 hours.

The reaction of this invention may be effected ordinarily by utilizing methods and apparatus which are conventionally used for known liquid phase reactions. The reaction is started ordinarily by preparing a mixture of organic halide and ketone, said mixture containing optionally some water, and adding thereto an aqueous solution of alkali metal hydroxide and nitrogen base catalyst in that order, or in reverse order. As long as the feeding of the alkali metal hydroxide and catalyst is completed in 5 to 30 minutes, hardly any difference in reaction results is observed according to the order of additon. As understood, the term "starting the reaction" as used in this invention means that the prescribed organic halide, ketone compound, alkali metal hydroxide, water and nitrogen base catalyst are supplied into the reaction system and the reaction mixture is regulated at the prescribed temperature. The term has no specific or critical meaning other than its normal one. A supplementary solvent or diluent is not necessary, but the reaction may be effected, if desired, in an additional solvent such as hexane or benzene without trouble.

The reaction is ordinarily continued until nearly all of the organic halide supplied is consumed. After the end of the reaction, the reaction mixture contains, as a precipitate, the alkali metal halide which is produced from the alkali metal hydroxide and the hydrogen halide, the latter being formed in situ by the reaction between the organic halide and the starting ketone. The product is separated from the reaction mixture by adding water thereto to dissolve the formed alkali metal halide and to decompose any remaining organic halide, separating the organic layer from the aqueous layer and evaporating the organic layer. In this case, the recovered raw ketone compound can be reused (i.e., recycled) as starting material. When the reaction mixture contains a comparatively lower boiling raw material such as acetone in the unreacted state, it can be separated from the reaction mixture by evaporating it at a pertinent time before separating the organic layer from the aqueous layer. In general, the produced ketone can be separated by filtering the reaction mixture containing the precipitated alkali metal halide to remove the solid, separating the filtrate into the organic layer and aqueous layer and distilling the organic layer. In this case, the separated aqueous layer can be recycled for reuse in the reaction or after distillation and/or supplying an alkali metal hydroxide, when required. In known methods wherein the reaction is effected by using solid alkali metal hydroxide under anhydrous conditions, it is very difficult to recover and reuse the alkali metal hydroxide, because a solid mixture of the unreacted alkali metal hydroxide with the alkali metal halide is present in the reaction mixture.

The starting organic halide and ketone compounds of this invention need not be especially active in their chemical structure and generally any organic halide capable of reaction with the active hydrogen-containing ketone compound can be used in this invention.

The organic halide may be, for example, an alkyl halide (e.g., methyl chloride, methyl bromide, ethyl chloride, ethyl bromide, propyl chloride, propyl bromide, butyl chloride, etc.); an alkenyl halide (e.g., 1-chloro-3-butene, citronellyl chloride, etc.); an allyl halide (e.g., allyl chloride, allyl bromide, methallyl chloride, crotyl chloride, 1-chloro-3-methyl-2-butene, 1-bromo-3-methyl-2-butene, 1,3-dichloro-2-butene, geranyl chloride, geranyl bromide, farnesyl chloride, phythyl chloride, etc.); a propargyl halide (e.g., propargyl chloride, propargyl bromide, etc.); a cycloalkyl halides (a cyclohexyl halide); or a benzyl halide; or the like. In addition, the corresponding iodides may be used.

As the starting ketone, there may be used any ketone having at least an active hydrogen atom at the $\alpha$-position to the carbonyl group. All of such compounds react with organic halides to produce the corresponding substituted ketone. Examples of the ketones are alkyl ketones (e.g., acetone, methyl ethyl ketone, diethyl ketone, methyl propyl ketone, methyl isobutyl ketone, ethyl butyl ketone, methyl amyl ketone, methyl isoamyl ketone, methyl hexyl ketone, etc.); alkenyl and cycloalkenyl ketones (e.g., mesityl oxide, allylacetone, methylheptenone, ionone, etc.), alicyclic ketones (e.g., cyclopentanone, cyclohexanone, cycloheptanone, etc.); camphor; acetophenone; and phenylacetone; and the like. The substituted ketones prepared by the reaction of the organic halide with the ketone are useful as various synthetic intermediates or perfumes. For example, methylheptenone, prepared by reacting prenyl chloride with acetone is particularly useful as a synthetic intermediate for preparing vitamin E and an intermediate to perfumes.

The present invention will be further illustrated by reference to the following examples, which are not intended to be limiting in any manner.

EXAMPLE 1

Into a three-necked flash (volume: 200 ml) equipped with a thermometer, a reflux condenser, and a stirrer, there were supplied 10.46 g of 1-chloro-3-methyl-2-butene (hereinafter referred to as "prenyl chloride"), 51 ml of acetone, powdery sodium hydroxide adjusted to make the mole ratio of water/prenyl chloride 0 to 10 or an aqueous solution of sodium hydroxide (3 mole equivalent for prenyl chloride and 0.348 g of stearyltrimethylammonium chloride (hereinafter referred to as STAC), and the resultant mixture was refluxed for 5 hours at 60°C. under vigorous stirring. After the end of the reaction, the reaction mixture was mixed with 40 ml of water to dissolve the precipitated sodium chloride. The methylheptenone in the organic layer was analyzed by gas chromatography, whereby the yield was obtained. Using each of triethylamine, monoethanolamine, benzylamine and ammonium chloride as a catalyst, the reaction was repeated under the same conditions in a catalyst amount of 1 mole % based on the number of moles of prenyl chloride as in the case of STAC. The results are shown in FIG. 1.

FIG. 1 shows the influence of the water content in the reaction system, having catalysts of different types, on the yield of methyl heptenone. In the reaction, methyl heptenone was produced by reacting prenyl chloride with acetone in the presence of alkali metal hydroxide.

The ordinate of the graph shown in this figure is the yield of methyl heptenone (%) and the abscissa is the molar ratio of $H_2O$/prenyl chloride at the start of the reaction. On the abscissa of FIG. 1, the integer 1 means that the reaction is started at a molar ratio of 1 mole of water to 1 mole of prenyl chloride, and the integer 10 indicates 10 moles of water and 1 mole of prenyl chloride.

As shown in said figure, when STAC was used as the catalyst in the reaction, methyl heptenone was obtained in high yields even in the reaction system, in which a large amount of water was already present at the beginning of the reaction, and the yield of methyl heptenone was not affected by the content of water in the system.

EXAMPLE 2

Using the same apparatus as in Example 1, there were supplied 10.46 g of prenyl chloride, 51 ml of acetone, 0.348 g of STAC and a 50% aqueous sodium hydroxide solution (1.5, 2, 3, and 4 mole equivalents based on prenyl chloride), and the resultant mixture was refluxed at 60°C. under vigorous stirring. The relation between the reaction time and the yield of methylheptenone for the respective mole ratios of sodium hydroxide to prenyl chloride was examined by adding n-decane to the reaction mixture before initiation as an interior standard for the gas chromatography analysis and sampling each at a constant reaction time. The results are shown in FIG. 2, where the curves are identified by the various sodium hydroxide/prenyl chloride molar ratios.

Figure 2:
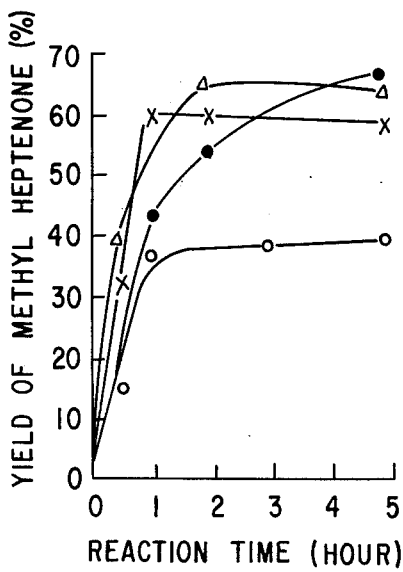

FIG. 2 shows the influence of the ratio of sodium hydroxide to prenyl chloride on the yield of methylheptenone in the production of methylheptenone by reacting prenyl chloride with acetone.

As shown in said figure, when the molar ratio of alkali metal hydroxide to organic halide is more than 2.0, the reaction product, i.e., methylheptenone, was obtained on good yield.

EXAMPLE 3

Figure 3:
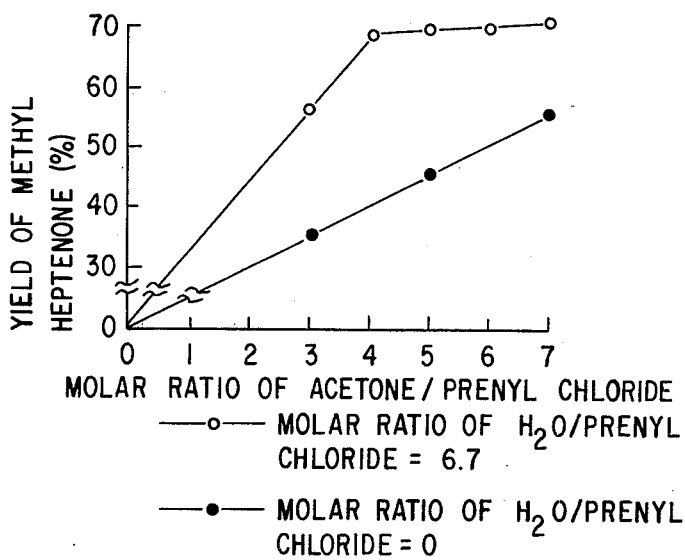

Using the same apparatus as in Example 1, there were supplied 10.45 g of prenyl chloride, 12 g of powdery sodium hydroxide, 0.07 g of STAC and acetone (3, 5 and 7 mole equivalents based on prenyl chloride), and then the resultant mixture was refluxed at 60°C. for 5 hours under vigorous stirring. The same reaction was repeated except that a 50% aqueous solution of sodium hydroxide was used in lieu of the powdery sodium hydroxide. After the reaction, methylheptenone was analyzed as in Example 1, and the yield was obtained. FIG. 3 shows the relation between the mole ratio of acetone to prenyl chloride and the yield of methylheptenone.

As shown in FIG. 3, the yield of methylheptenone is affected by both the molar ratio of water to prenyl chloride, and the molar ratio of acetone to prenyl chloride.

EXAMPLE 4

Figure 4:
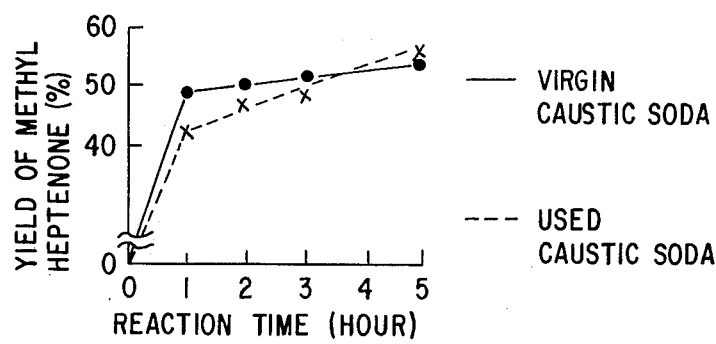
FIG. 4 shows the relationship between reaction time and yield for fresh alkali metal hydroxide and reused alkali metal hydroxide.

Using the same apparatus as in Example 1, there were supplied 10.45 g of prenyl chloride, 51 ml of acetone, 24 g of a 50% aqueous solution of sodium hydroxide and 0.348 g of STAC, and the resultant mixture was refluxed at 60°C. for 5 hours under vigorous stirring. After the end of the reaction, the reaction mixture was mixed with 40 ml of water to dissolve the precipitated sodium chloride. The aqueous layer was separated and concentrated by heating to remove 46 ml of water. The concentration of sodium hydroxide in the concentrated aqueous solution was titrated with 5 N hydrochloric acid and found to be 50.6%. This aqueous solution of sodium hydroxide (8 g) was mixed with a 50% aqueous solution of sodium hydroxide (4 g), and the same reaction was repeated. As in Example 3, the relation between the reaction time and the yield of methylheptenone was examined in each reaction. FIG. 4 shows the results.

EXAMPLE 5

Figure 5:
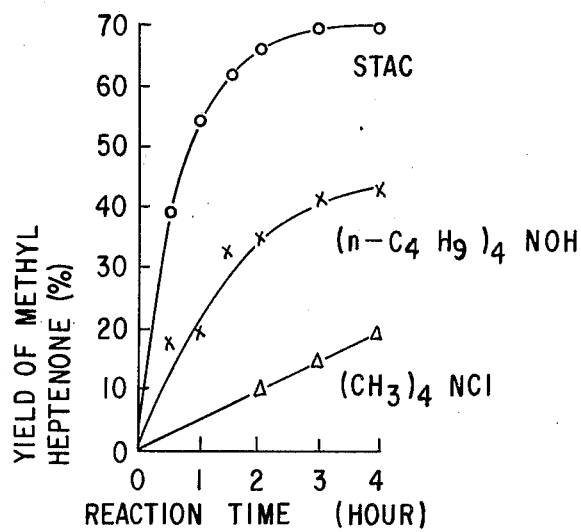
FIG. 5 shows the effects on yield using different catalysts.

Using the same reaction apparatus as in Example 1, there were supplied 10.45 g of prenyl chloride, 51 ml of acetone, a 50% aqueous solution of sodium hydroxide (24 g), 5 ml of n-decane (Interior standard for the gas chromatography) and 0.348 g of STAC (0.348 g), and the resultant mixture was refluxed at 60°C. for 5 hours under vigorous stirring. The same reaction was repeated except that a 10% aqueous solution of tetrabutylammonium hydroxide and tetramethylammonium chloride (control) were used in amounts of 1 mole % based on prenyl chloride in lieu of STAC. The relation between the reaction time and the yield of methylheptenone was examined in each reaction, and results are shown in FIG. 5.

EXAMPLE 6

Using the same apparatus as in Example 1, there were supplied 10.45 g of prenyl chloride, 51 ml of acetone, 12 g of powdery sodium hydroxide and 0.101 g of triethylamine, and the resultant mixture was refluxed at 60°C. for 5 hours under vigorous stirring. After the end of the reaction, methylheptenone was analyzed by gas chromatography as in Example 1, and the yield was examined. For observing the reproducibility of the results of the reaction, the same reaction was repeated 5 times.

The same reaction was repeated except that a 50% aqueous sodium hydroxide solution (24 g) was used in lieu of the powdery sodium hydroxide. The same reaction was repeated under anhydrous conditions and with a 50% aqueous sodium hydroxide solution except that 0.348 g of STAC was used in lieu of triethylamine. In every case the same reaction was repeated 5 times. Results were obtained by squaring the remainder between the average yield of methylheptenone in 5 repetitions and the yields in individual reactions and figuring out the sum of each squared value. A smaller figure in Table 1 shows a better reproducibility of results of the reaction.

Table 1

| $\dfrac{H_2O}{NaOH+H_2O} \times 100$ | Catalyst used | Average yield of methyl-heptanone ($\overline{mH}$, %) | $\sum_{N=1}^{5} (\overline{mH}-mH_n)^2$ |
|---|---|---|---|
| 0 | $Et_3N$ | 37.9 | 628.2 |
| | STAC | 54.3 | 202.5 |
| 50 | $Et_3N$ | 47.4 | 27.6 |

Table 1-continued

| $\dfrac{H_2O}{NaOH+H_2O} \times 100$ | Catalyst used | Average yield of methyl-heptanone (mH, %) | $\sum_{N=1}^{5} (mH-mH_n)^{2*}$ |
|---|---|---|---|
|  | STAC | 63.5 | 21.3 |

*$\overline{mH}$ and mH represent the average yield of methylheptenone and the yield in the individual reactions, respectively.

EXAMPLE 7

In a stainless reactor (volume: 180l) there were supplied 20.7 kg of 1,4-prenyl chloride, a 50 % aqueous sodium hydroxide solution (47.48 kg), 65l of acetone and 137.6 g of STAC, and the resultant mixture was refluxed at 60°C. for 6 hours under stirring. After the end of the reaction the reaction mixture was mixed with 55 kg of water to dissolve the precipitated sodium chloride and evaporated to remove the acetone. The organic layer was separated from the aqueous layer and distilled under reduced pressure to give a distillate (15.47 kg) boiling at 105°C./100 mg Hg as a main distillate. This was assayed by gas chromatography and found to be a pure methylheptenone. The yield was 62 %.

EXAMPLES 8 TO 23

Using the same apparatus as in Example 1, there were supplied 10.45 g of prenyl chloride, 30 g of acetone, a 50 % aqueous sodium hydroxide solution (32.0 g) and 0.005 mole of the subsequent catalysts, and the resultant mixture was refluxed at 60°C. for 3 hours. The results are shown as follows:

| Example No. | Catalyst Used | Yield of Methyl-heptenone (%) |
|---|---|---|
| 8 | $[C_{12}H_{25}N(CH_3)_2-CH_2-C_6H_5]^+Cl^-$ | 54.5 |
| 9 | $C_{18}H_{37}N^+(CH_3)_2-CH_2COO^-$ | 36.2 |
| 10 | $[C_{18}H_{37}CONHC_3H_6N(CH_3)(C_2H_4OH)]^+NO_3^-$ | 46.9 |
| 11 | $C_{18}H_{37}CONHC_2H_4NHC_2H_4OH \cdot CH_3CH(OH)COOH$ | 47.1 |
| 12 | $[C_{12}H_{25}N(C_2H_4OH)_2]HCl$ | 38.0 |
| 13 | $C_{12}H_{25}NH_2$ | 37.3 |
| 14 | $C_6H_{11}NH_2$ | 13.0 |
| 15 | $(C_6H_5)_3N$ | 10.3 |
| 16 | $CH_3N(C_6H_5)_2$ | 8.9 |
| 17 | $C_{12}H_{25}{}^+N(CH_3)_2-CH_3 \cdot Cl^-$ | 61.0 |
| 18 | $C_{12}H_{25}-N^+(CH_3)_2-C_2H_5 \cdot Cl^-$ | 63.2 |
| 19 | $C_{16}H_{37}-N^+(CH_3)_2-C_2H_5Br^-$ | 68.7 |
| 20 | $C_{16}H_{33}-N^+(CH_3)_2-CH_3Br^-$ | 62.5 |
| 21 | $[C_{16}H_{33}N(CH_3)_2-CH_2-C_6H_5]^+Cl^-$ | 63.7 |
| 22 | $(C_4H_9)_2NH \cdot HCl$ | 32.4 |

| Example No. | Catalyst Used | Yield of Methyl-heptenone (%) |
|---|---|---|
| 23 | $(C_4H_9)_3N \cdot HCl$ | 35.6 |

EXAMPLE 24

154.3 g of linalool was mixed with 250 ml of concentrated hydrochloric acid at 5°C. 100 ml of heptane was added thereto, and the resultant mixture was separated. The organic layer was washed thrice with 50 ml of water, and mixed with 407 g of acetone, 160 g of sodium hydroxide, 160 ml of water and 7.0 g of STAC. The resultant mixture was refluxed for 3 hours at 60°C. The reaction mixture was mixed with 300 ml of water, separated from the aqueous layer, and distilled under reduced pressure to give 83.5 g of geranylacetone. The yield was 43 %.

EXAMPLE 25

In an autoclave (volume: 500 ml), there were supplied 72.1 g of methyl ethyl ketone, 19.1 g of allylchloride, a 50% aqueous sodium hydroxide solution (80 g), and 1.3 g of lauryltrimethylammonium chloride in that order, and the resultant mixture was heated at 65°C. for 4 hours. The reaction mixture was assayed by gas chromatography, whereby the production of 12.8 g of 3-methylpentene-1-4-one was found. The yield was 52 %.

EXAMPLE 26

By using the same reaction vessel as used in Example, 1, 10.45 g of prenyl chloride, 19.6 g of mesityl oxide, 24 g of a 50 % aqueous caustic soda solution and 0.348 g of STAC were added into the vessel, and the mixture was allowed to react for 5 hours at 90°C. with stirring, After the reaction was completed, 10 ml of water was added to dissolve the sodium chloride which had been precipitated off from the reaction. The water layer of said solution was separated from the organic layer was distilled. The following fractions of distillate were obtained.

| Fraction No. 1 | 62 °C./3 mmHg | 7.63 g |
| Fraction No. 2 | 72.5 °C./3 mmHg | 5.48 g |

These fractions were analyzed using I.R. (infrared ray analysis), NMR (nuclear molecular resonance) and mass spectrograph. No. 1 was found to be β-isopentenyl mesityl oxide and No. 2 α-isopentenyl mesityl oxide, respectively. The yield of said reactions was 46 % and 33 %, respectively.

EXAMPLE 27

By using the same reaction vessel as used in Example 1, 10.45 g of prenyl chloride, 34.8 ml of acetone, 20.3 g of a 65 % aqueous caustic soda solution, 5 ml of n-decane and 0.264 g of lauryl trimethylammonium chloride were added into the vessel, and then the mixture was allowed to react for 12 hours at 30°C. with vigorous stirring. After the reaction was completed, 40 ml of water was added to the resultant solution to dissolve the sodium chloride. Methyl heptenone was produced as determined by using gas chromatography and the yield was 51 % calculated on the theoretical value.

EXAMPLE 28

By using the same reaction vessel as used in Example 1, 10.89 g ethyl bromide, 34.8 ml of acetone, 24 g of a 50 % caustic soda solutiin and 0.348 g of STAC were added into the vessel and then the mixture was allowed to react for 5 hours at 60°C. with vigorous stirring. After the reaction was completed, 5 ml of n-heptane was added, as the internal standard of the gas-chromatography, and then the product was determined by the gas chromatography. The yield of methyl propyl ketone was 30.5% calculated on the theoretical value.

While the invention has been described with reference to preferred embodiments thereof, it is to be understood that various changes and modifications may be made without departing from the spirit and scope of the invention as defined by the appended claims.

WHAT WE CLAIM:

1. In a catalytic process for producing a substituted ketone by reacting an organic halide selected from the group consisting of alkyl halides, alkenyl halides, allyl halides, propargyl halides, cyclo alkyl halides and benzyl halides and a ketone having a replaceable hydrogen atom on the carbon atom which is in he α-position to the carbonyl group thereof and selected from the group consisting of alkyl ketones, alkenyl ketones, cyclo alkenyl ketones, alicyclic ketones and aryl ketones, in the presence of a catalyst and an alkali metal hydroxide, the improvement which comprises said reaction being conducted in water, wherein the catalyst is selected from the group consisting of 1. Primary amines having the general formula:

$$R_1NH_2$$

wherein said $R_1$ is an unsubstituted or substituted alkyl group having at least 4 carbon atoms and the acid salts thereof;

2. primary amines having the general formula:

$$Z-(CH_2)_n-NH_2$$

wherein Z is a hydroxyl group or an amino group and n represents the integer 2 or 3, and the acid salts thereof;

3. secondary amines having the general formula:

$$R_2R_3NH$$

wherein said $R_2$ and $R_3$ each represents an alkyl unsubstituted or substituted alkyl group, a cycloalkyl group having at least 6 carbon atoms, or an aralkyl group having at least 7 carbon atoms, with the proviso that said $R_2$ and $R_3$ may not simultaneously be methyl, and the acid salts thereof;

4. tertiary amines having the general formula:

wherein said $R_4$, $R_5$ and $R_6$ each represents an unsubstituted or substituted alkyl group, a cycloalkyl group having at least 7 carbon atoms, with the proviso that said $R_4$, $R_5$ and $R_6$ may not simultaneously be methyl, and the acid salts thereof;

5. quaternary ammonium salts having the general formula:

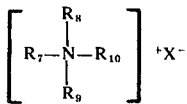

wherein said $R_7$, $R_8$, $R_9$ and $R_{10}$ each represents a substituted or unsubstituted alkyl group, a cycloalkyl group having at least 6 carbon atoms, or an aralkyl group having at least 7 carbon atoms, with the proviso that said $R_7$, $R_8$ $R_9$ and $R_{10}$ may not simultaneously be methyl, and the acid salts thereof, and wherein $X^-$ is an inorganic or organic anion;

6. betaine-type quaternary ammonium salts having the general formula:

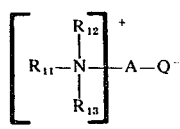

wherein said $R_{11}$, $R_{12}$ and $R_{13}$ each represents a substituted or unsubstituted alkyl group, with the proviso that said $R_{11}$, $R_{12}$ and $R_{13}$ may not simultaneously be methyl, —A— is an alkylene group and $Q^-$ is —$SO_3^-$ or —$COO^-$; and 7. mixtures thereof;

i. wherein each substituentt of $R_1$, $R_2$, $R_3$, $R_4$, $R_5$, $R_6$, $R_7$, $R_8$, $R_9$ and $R_{10}$ is hydroxy, amino, alkoxy or acyl and each substituent of $R_{11}$, $R_{12}$ and $R_{13}$ is hydroxy, amine, alkoxy, acyl or acyloxy; and
  ii. wherein the salts of said primary amines (1 and 2), said secondary amine (3), and said tertiary amine (4) are hydrochloride, nitrate, sulfate, phosphate and acetate thereof and the anion of said quaternary ammonium salts is selected from the group consisting of $cl^-$, $Br^-$, $I^-$, $OH^-$, $NO_3^-$,

 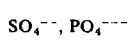

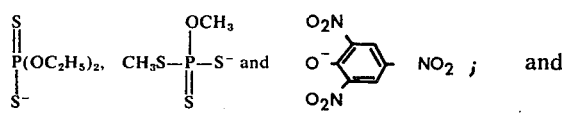

iii. wherein the molar ratio of water/organic halide is at least 2,5; and
  iv. wherein the molar ratio of alkali metal hydroxide/water is at least 0.3; and
  v. wherein the molar ratio of alkali metal hydroxide/organic halide is at least 2,0.

2. The process of claim 1, wherein said catalyst is a quaternary ammonium salt having the general formula:

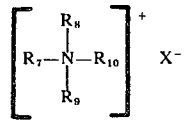

wherein each of $R_7$, $R_8$, $R_9$ and $R_{10}$ is selected from the group consisting of an alkyl group having from 8 to 20 carbon atoms, a cycloalkyl group having 6 to 12 carbon atoms, or an aralkyl group having 7 to 12 carbon atoms, and X is selected from the group consisting of $Cl^-$, $Br^-$, $I^-$, $OH^-$ and $NO_3^-$.

3. The process of claim 1, wherein said catalyst is selected from the group consisting of cetyltrimethylammonium salts, cetyldimethylethylammonium salts, lauryldimethylammonium salts, stearyltrimethylammonium salts, stearyldimethylethylammonium salts, benzyltrimethylammonium salts and benzyldimethylethylammonium salts.

4. The process of claim 1, wherein said catalyst is

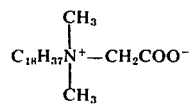

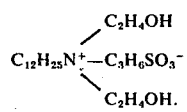

5. The process of claim 1, wherein said organic halide is an alkyl halide.

6. The process of claim 1, wherein said organic halide is an alkenyl halide.

7. The process of claim 1, wherein said organic halide is an allyl halide.

8. The process of claim 1, wherein said organic halide is 1-chloro-3methyl-2-butene.

9. The process of claim 1, wherein said organic halide is a propargyl halide.

10. The process of claim 1, wherein said organic halide is a cyclohexyl halide or a benzyl halide.

11. The process of claim 1, wherein said ketone is an alkyl ketone.

12. The process claim 1, wherein said ketone is acetone.

13. The process of claim 1, wherein said ketone is methyl ethyl ketone.

14. The process of claim 1, wherein said ketone is an unsaturated ketone.

15. The process of claim 1, wherein said ketone is an alicyclic ketone.

16. The process of claim 1, wherein said ketone is camphor, acetophenone, or phenyl acetone.

17. The process of claim 1, wherein the temperature of reation is from 0° C. to 150°C.

18. The process of claim 1, wherein the molar ratio of said organic halide to said ketone is from 2/1 to 1/30.

19. The process of claim 1, wherein said catalyst is present in an amount of 0.05 to 20 mole % based on the number of moles of said organic halide.

20. The process of claim 3, wherein said catalyst is present in an amount of 0.01 to 1 mole % based on the number of moles of said organic halide.

21. The process of claim 1, wherein the molar ratio water/organic halide is from 2.5 to 10; wherein the molar ratio alkali metal hydroxide/organic halide is from 2.5 to 4; and wherein the molar ratio alkali metal hydroxide/water is from 0.35 to 0.85.

22. The process of claim 1, wherein said reaction is conducted until substantially all of said organic halide is converted into said substituted ketone.

23. In a catalytic process for producing methylheptenone by reacting prenyl chloride and acetone in the presence of a catalyst and an alkali metal hydroxide, the improvement which comprises said reaction being conducted in water, wherein the catalyst is stearyltrimethylammonium chloride, wherein the molar ratio water/prenyl chloride is at least 2.5, wherein the molar ratio alkali metal hydroxide/water is at least 0.3 and wherein the molar ratio alkali metal hydroxide/prenyl chloride is at least 2.0.

* * * * *

UNITED STATES PATENT OFFICE
CERTIFICATE OF CORRECTION

Patent No. 3,983,175  Dated September 28, 1976

Inventor(s) Yoshin Tamai, Takashi Nishida, Fumio Mori, Yoshiaki Omura, Masahisa Tanomura, Takeo Hosogai, Yoichi Ninagawa and Kazuo Itoi It is certified that error appears in the above-identified patent and that said Letters Patent are hereby corrected as shown below:

The following statement for convention priority should be inserted into the bibliographic column:

-- [30] Foreign Application Priority Data
  Nov. 17, 1972    Japan ---- 47-115989
  Aug.  9, 1973    Japan ---- 48- 89861

Column 5, lines 35-37,

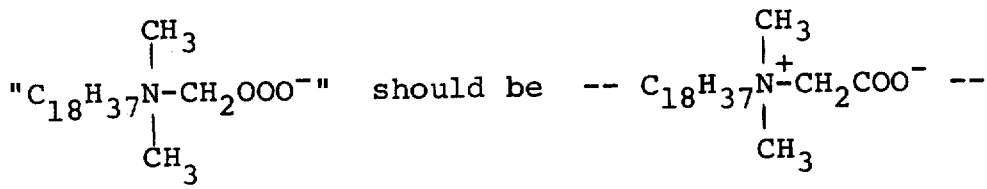

Column 5, line 60, "shoe" should read as -- show --.

Column 12, Example 21,

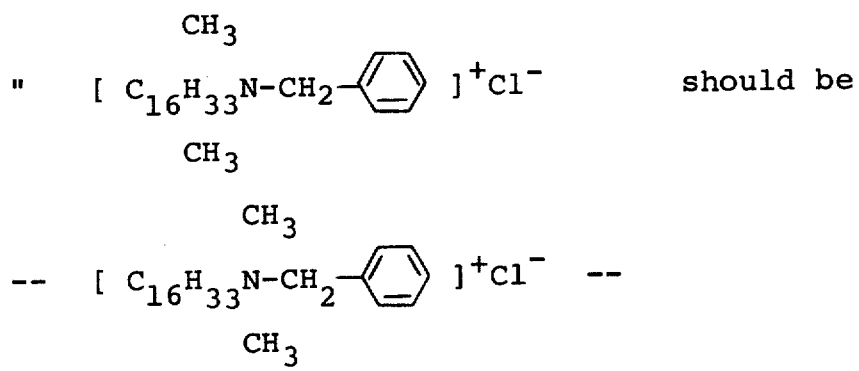

Column 14, line 33, "he" should read -- the --.

UNITED STATES PATENT OFFICE
CERTIFICATE OF CORRECTION

Patent No. 3,983,175  Dated September 28, 1976

Inventor(s) Yoshin Tamai, Takashi Nishida, Fumio Mori, Yoshiaki Omura, Masahisa Tanomura, Takeo Hosogai, Yoichi Ninagawa and Kazuo Itoi It is certified that error appears in the above-identified patent and that said Letters Patent are hereby corrected as shown below:

Column 14, line 56, "alkyl" should be canceled.

Column 15, line 48, "cl" should be -- Cl --.

Column 16, line 16, "X" should read -- $X^-$ --.

Signed and Sealed this

Nineteenth Day of April 1977

[SEAL]

Attest:

RUTH C. MASON
*Attesting Officer*

C. MARSHALL DANN
*Commissioner of Patents and Trademarks*